(12) United States Patent
Tauber et al.

(10) Patent No.: US 8,361,492 B2
(45) Date of Patent: *Jan. 29, 2013

(54) DRUG DELIVERY SYSTEM AND METHODS OF USE

(75) Inventors: Shachar Tauber, Ozark, MO (US); Randall Fuerst, Orangevale, CA (US); Keela Davis, Springfield, MO (US); Lyle Bowman, Pleasanton, CA (US); Gary Wnek, Cleveland, OH (US); Joseph J. Bango, Jr., New Haven, CT (US)

(73) Assignee: Ocugenics, LLC, Orangevale, CA (US)

( * ) Notice: Subject to any disclaimer, the term of this patent is extended or adjusted under 35 U.S.C. 154(b) by 493 days.

This patent is subject to a terminal disclaimer.

(21) Appl. No.: 12/490,972

(22) Filed: Jun. 24, 2009

(65) Prior Publication Data

US 2009/0269392 A1 Oct. 29, 2009

Related U.S. Application Data (63) Continuation-in-part of application No. 12/416,802, filed on Apr. 1, 2009, now Pat. No. 8,083,347.

(60) Provisional application No. 61/125,985, filed on Apr. 29, 2008.

(51) Int. Cl.
*A61F 13/00* (2006.01)
*A61K 9/00* (2006.01)

(52) U.S. Cl. .................................... 424/443; 424/429

(58) Field of Classification Search ............... 424/429
See application file for complete search history.

(56) References Cited

U.S. PATENT DOCUMENTS

| | | | |
|---|---|---|---|
| 2003/0017208 A1* | 1/2003 | Ignatious et al. | 424/486 |
| 2003/0193118 A1 | 10/2003 | Bango et al. | |
| 2003/0215624 A1 | 11/2003 | Layman et al. | |
| 2003/0232287 A1 | 12/2003 | Bango | |
| 2004/0018226 A1 | 1/2004 | Wnek et al. | |
| 2005/0067287 A1 | 3/2005 | Fuerst et al. | |
| 2006/0085063 A1* | 4/2006 | Shastri et al. | 623/1.41 |
| 2006/0171991 A1 | 8/2006 | Bango | |
| 2006/0246113 A1 | 11/2006 | Griffith et al. | |
| 2008/0002149 A1 | 1/2008 | Fritsch et al. | |
| 2009/0217849 A1 | 9/2009 | Eastin et al. | |
| 2009/0238858 A1 | 9/2009 | Kohn et al. | |

OTHER PUBLICATIONS

Office Action issued in related U.S. Appl. No. 12/416,802, dated Sep. 17, 2010, 11 pages.
International Search Report and Written Opinion issued in PCT/US2010/029126, dated Jan. 14, 2011, 11 pages.
Kenawy, E.R, et al. "Controlled Release of Ketoprofen from electrospun poly(vinyl alcohol) nanofibers" Materials Science & Engineering A 459, pp. 390-396, 2007.
Huang, Z.M., et al. "A review on polymer nanofibers by electrospinning and their applications in nanocomposites," Composites Science & Terchnology 63, pp. 2223-2253, 2003.

* cited by examiner

*Primary Examiner* — Frederick Krass
*Assistant Examiner* — Dennis J Parad
(74) *Attorney, Agent, or Firm* — Lathrop & Gage LLP (57) ABSTRACT

Electrospun fibers are utilized to improve the mechanical characteristics of a contact lens reducing the weight and mechanical strength of the polymers from which the lenses are typically formed. Electrospun fibers are also utilized as a drug delivery system, both through direct use in the eye and by inclusion of the fibers in a contact lens. The fibers are loaded with therapeutic drugs by a variety of methods and processed by coating and cross-linking the fibers.

25 Claims, 8 Drawing Sheets

DRUG DELIVERY SYSTEM AND METHODS OF USE

CROSS-REFERENCE TO RELATED APPLICATIONS

This is a continuation-in-part application which claims priority of U.S. Non-provisional patent application Ser. No. 12/416,802 filed on Apr. 1, 2009, now issued as Pat. No. 8,083,347, which claims priority of U.S. Provisional Patent Application No. 61/125,985 filed on Apr. 29, 2008, which applications are incorporated herein by reference.

BACKGROUND

Field of the Invention

Electrospun polymer fibers provide a material with a variety of favorable characteristics that may be tailored to fit various applications. The fibers in the electrospun materials provide superior mechanical strength with reduced weight and volume. They also have high surface area and porosity which may be altered as desired during fabrication.

It is therefore desirable to provide a drug delivery system utilizing electrospun polymer fibers. The drug delivery system may utilize the fibers for insertion directly into the eye maintaining the concentration of the drug in the eye at an efficacious level throughout the period of drug delivery.

The system may also utilize an improved contact lens incorporating electrospun fibers with desired characteristics, and a system and method for delivering ophthalmic drugs from the improved contact lens to an eye over an extended period of time while maintaining the concentration of the drug in the eye at an efficacious level throughout the period of drug delivery.

It is also desirable to provide a system and method for preloading drugs in the delivery system in a manner that allows the delivery system to be stored for an extended period of time.

SUMMARY OF THE INVENTION

The drug delivery system described herein utilizes both "raw" electrospun fibers and an improved contact lens as the means of drug delivery. The fibers and the improved contact lens provide a drug delivery system comprising a drug-releasing scaffold formed from a mat of electrospun fibers and methods for incorporating various therapeutic drugs into the mat. The fiber mat may be utilized directly in the eye for delivery of drugs, or incorporated into an improved contact lens.

The therapeutic drugs may be loaded into the drug delivery system by soaking the electrospun mats in a solution containing the drug, or by providing the drugs in the solution feeding the electrospinning process thus incorporating the drug into the fibers in the electrospun mat. Various processes for treating the electrospun mats after loading with therapeutic drugs are also described for improving the drug delivery characteristics, such as coating the mats in a polymer and cross-linking the electrospun fibers.

The improved contact lens described herein also comprises a contact lens that incorporates electrospun fibers to provide desirable physical characteristics. The improved contact lens may be fabricated with a thinner cross-section due to the increased mechanical strength and rigidity of the electrospun fiber materials. The thinner cross-section lens provides increased oxygen permeability while maintaining mechanical strength.

DETAILED DESCRIPTION

Electrospun Fiber Mat Fabrication

The electrospun fiber mat used in the present invention is fabricated by polymerizing electrospun fibers and loading a therapeutic drug in the fiber mat using a variety of techniques, which are described below with examples.

The electrospinning process typically comprises an apparatus including one or more electrically-conducting liquid dispenser, such as a stainless steel needle, disposed adjacent to a collector. The liquid dispenser is held at a high electric potential, or voltage, with respect to the collector. The electric potential may be either alternating current (AC) or direct current (DC), or a DC biased AC voltage. Alternatively, a substrate for receiving the electrospun fibers may be inserted between the conducting dispenser and the collector such that the fibers will be deposited on the substrate as they are propelled from the liquid dispenser by the electric field toward the collector.

A solution source, or well, containing a solution of the polymer and various other components which may include a polymer precursor (monomer) is attached to the electrically-conducting liquid dispenser by a fluid conducting element such as a short tube. The polymer solution is propelled through the dispenser at a predetermined rate, either by gravity or by mechanical means such as a pump. As the solution is dispensed through the electrically-conducting dispenser, the high electric potential between the dispenser and the collector leads to the formation of uniform fibers which are deposited on the collector. The fibers may be micro-fibers or nano-fibers depending on the parameters of the electrospinning process. As the fibers are deposited on the collector they overlap to form a mat, as further described below.

Polymer solutions for use in the fiber mat fabrication disclosed herein include, but are not limited to, aqueous solutions having between 5 and 15 percent polymer by weight.

Various additives may be added to the precursor solution to lower surface tension, or to otherwise alter the characteristics of the solution or the electrospun fibers as desired. For example, surfactants, such as Triton X-100, poloxomer 407 or other suitable surfactant, may be added to the precursor solution to lower the surface tension of the solution.

Polymers for use in the electrospinning process include, but are not limited to the following: poly(2-hyroxyethylmethacrylate) (pHEMA), poly(acrylic acid) (PAA), poly(methacrylic acid), poly(Vinyl pyrolidone) (PVP), poly(N-vinyl pyrolidone) (PVP), Polyvinyl alcohol (PVA), poly(methyl methacylate) (PMMA), poly(glyceral methacrylate) (PGMA), Silicone Hydrogels, Fluorocarbon hydrogels, polyacrylamide (PAM), Silicone and 3-methacryloxy-2 hydroxypropyloxy)propylbis(trimethylsiloxy)methylsilane. Other polymers may be utilized if soluble in a solvent such as water, methanol, ethanol, hexane, acetonitrile, or tetrahydrofuran to allow the electrospinning process. If the fibers are to be utilized in a contact lens as described below, the fibers are preferably formed from a polymer that is the same as the polymer to be used in the remainder of the contact lens, or a polymer that has a similar index of refraction, to reduce negative optical characteristics of the improved contact lens. Additional polymer precursor solutions are described below.

As the fibers are deposited on the collector they form a mat of overlaying fibers. In some methods of depositing the fibers, the collector is translated in one or more linear dimensions, or in a rotational or orbital manner, perpendicular to the direction of fiber deposition to increase the area over which the fibers are deposited and to improve the consistency of the fiber mat.

After a desired period of deposition, a fiber mat of a certain thickness will be formed, and can be removed from the electrospinning apparatus and prepared for further processing.

After deposition, the fiber mat may be processed in several ways to improve the characteristics of the fiber mat. The fiber mat may be coated with a polymer by exposing the mat to an solution of polymer precursor. As described below, coating the fiber mat alters the characteristics of the fiber mat, including the release of drugs incorporated in the fiber mat. After any chemical processing, the mats may be further processed by cutting into sections or grinding into particles.

The fiber mats may also be processed by exposing them to a crosslinking agent such as ethylene glycol dimethacrylate (EGDMA), tetraetheylene glycol dimethacrylate (TEGDMA), divinyl benzene (DVB), divinylacrylamide (DVACR), or any tri-allyl crosslinking agent. Methanol may be added to PVA to crosslink the polymer. The crosslinking process increases the mechanical stability of the fiber mat by linking adjacent fibers as they intersect randomly in the fiber mat.

An example process for creating an electrospun fiber mat is as follows.
1. Combine the following materials, mix, place over heat and stir inside round-bottom flask with attached condenser for 6.5 hours.
   10 wt % PPVA+2 wt % Triton X-100+DI water
   11.363 g Polyvinyl alcohol (Sigma-Aldrich 99% hydrolyzed)
   2.277 g Triton X-100 (Aldrich)
   27.539 g Ultra high purified water added to Triton X-100 (Elgan)
   72.459 g Ultra high purified water added to PVA (Elgan)
   This is the PVA polymer mixture. Without allowing the polymer mixture to cool performing the following steps.
2. Add 2.000 ml of Vigamox to 14.141 g of the PVA polymer mixture and vortex stir for 1 minute.
3. Add 7.0 ml of the PVA/Vigamox solution to 2 syringes for a total of 14.0 ml of solution.
4. Electrospin the PVA/Vigamox solution from both needles simultaneously at the following parameters:
   Dispense rate: 1.8 ml/hr
   18 gauge blunt end needles
   Voltage: 30 kV
   Travel distance: 4 in
   Total time: 2.5 hours
5. After electrospinning, the resulting mat is cut into approximately 3.0 mg squares.
6. If crosslinking is desired, soak the squares in methanol for 7 hours and allow to air dry in ambient conditions overnight.
7. Coat the squares in the remaining PVA polymer solution created in step 1 above. Before coating the squares, the PVA polymer solution is heated in a round bottom flask with attached condenser for 2 hours.
8. After coating the squares in the polymer solution, allow them to air dry in ambient conditions overnight.
9. If a second cross-link is desired soak the squares in methanol for 7 hours and then allow them to air dry in ambient conditions overnight.

When measuring drug release profiles the following procedure was utilized:
1. Each sample mat was placed into 0.5 ml ISO 18369 saline solution in cuvettes.
2. Absorbance measurements were taken at 1, 5, 10, 20, 60, 1440, and 2880 minutes by removing the sample mat with tweezers and measuring the absorbance at 336 nm. Sample mats were immediately placed back in the sample cuvette after measurement.
3. Measurements were normalized by mass of the sample mat prior to dip-coating.

Polymer Materials for Electrospun Fibers

Suitable hydrophobic comonomers (a) for use in electrospun fibers include, without this list being exhaustive, $C_1$-$C_{18}$alkyl and $C_3$-$C_{18}$cycloalkyl acrylates and methacrylates, $C_3$-$C_{18}$alkylacrylamides and -methacrylamides, acrylonitrile, methacrylonitrile, vinyl $C_1$-$C_{18}$alkanoates, $C_2$-$C_{18}$alkenes, $C_2$-$C_{18}$haloalkenes, styrene, lower alkyl styrene, lower alkyl vinyl ethers, $C_2$-$C_{10}$ perfluoroalkyl acrylates and methacrylates or correspondingly partly fluorinated acrylates and methacrylates, $C_3$-$C_{12}$ perfluoroalkyl-ethyl-thiocarbonylaminoethyl acrylates and methacrylates, acryloxy- and methacryloxy-alkylsiloxanes, N-vinylcarbazole and $C_1$-$C_{12}$alkyl esters of maleic acid, fumaric acid, itaconic acid, mesaconic acid and the like. Preferred comonomers are, for example, acrylonitrile, $C_1$-$C_4$alkyl esters of vinylically unsaturated carboxylic acids having 3 to 5 carbon atoms, or vinyl esters of carboxylic acids having up to 5 carbon atoms.

Examples of suitable hydrophobic comonomers (a) include methyl acrylate, ethyl acrylate, propyl acrylate, isopropyl acrylate, isobutyl acrylate (IBA), isooctyl acrylate (OA), isodecyl acrylate (DA), cyclohexyl acrylate, 2-ethylhexyl acrylate (EHA), methyl methacrylate, ethyl methacrylate, propyl methacrylate, butyl acrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethylthiocarbonylaminoethyl methacrylate, isobornyl methacrylate, trifluoroethyl methacrylate, hexafluoroisopropyl methacrylate, hexafluorobutyl (meth)acrylate (HFBMA and HFBA), tris-trimethylsilyloxysilyl-propyl methacrylate (TRIS), 3-methacryloxypropylpentamethyldisiloxane and bis(methacryloxypropyl) tetramethyldisiloxane. Preferred examples of hydrophobic comonomers (a) are methyl methacrylate, IBA, HFBA, HFBMA, OA, EHA, DA, TRIS and acrylonitrile. Suitable hydrophilic comonomers (a) include, without this list being conclusive, hydroxyl-substituted lower alkyl acrylates and methacrylates, acrylamide, methacrylamide, lower alkylacrylamides and -methacrylamides, ethoxylated acry-lates and methacrylates, hydroxyl-substituted lower alkylacrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino-lower alkyl (where the term "amino" also includes quaternary annnononium), mono-lower alkylamino-lower alkyl and di-lower alkylamino-lower alkyl acrylates and methacrylates, allyl alcohol and the like. Preferred comonomers are, for example, N-vinyl-2-pyrrolidone, acrylamide, methacrylamide, hydroxyl-substituted lower alkyl acrylates and methacrylates, hydroxyl-substituted lower alkylacrylamides and -methacrylamides and vinylically unsaturated carboxylic acids having a total of 3 to 5 carbon atoms. Examples of suitable hydrophilic comonomers (a) include hydroxyethyl methacrylate (HEMA), hydroxyethyl acrylate, hydroxypropyl acrylate, trimethylammonium-2-hydroxy-ypropyl methacrylate hydrochloride (Blemer® MQA, for example from Nippon Oil), dimethylaminoethyl meth acrylate (DMAEMA), dimethylaminoethyl methacrylamide, acrylamide, methacrylamide, N,N-dimethylacrylamide (DMA), allyl alcohol, vinylpyridine, glycerol methacrylate, N-(1,I-dimethyl-3-oxobutyl)acrylamide, N-vinyl-2-pyrrolidone (NVP), acrylic acid, methacrylic acid and the like. Preferred hydrophilic comonomers (a) are 2-hydroxyethyl methacrylate, dimethylaminoethyl methacrylate, trimethylammonium-2-hydroxypropyl methacrylate hydrochloride, N,N-dimethylacrylamide and N-vinyl-2-pyrrolidone.

The polymers according to the invention are built up in a known manner from the corresponding monomers (the term monomers here also including a macromer according to the invention) by a polymerization reaction with which the expert is familiar. Usually, a mixture of the abovementioned monomers is heated, with the addition of an agent which forms free radicals. Such an agent which forms free radicals is, for example, azoisobutyronitrile (AIBN), potassium peroxodisulfate, dibenzoyl peroxide, hydrogen peroxide or sodium percarbonate. If the compounds mentioned are heated, for example, free radicals are then formed, by homolysis, and can then, for example, initiate a polymerization.

A polymerization reaction can be carried out using a photoinitiator. Photopolymerization is the term used in this case. For photopolymerization, a photoinitiator which can initiate free radical polymerization and/or crosslinking by the use of light is suitably added. Examples of this are familiar to the expert, and specifically, suitable photoinitiators are benzoin methyl ether, I-hydroxycyclohexyl phenyl ketone and Darocur and Irgacur types, preferably Darocur 11738® and Darocur 29590®. Reactive photoinitiators which can be incorporated, for example, into a macromer or can be used as a special comonomer (a) are also suitable. Examples of these are to be found in EP 632 329. The photopolymerization can then be triggered off by actinic radiation, for example light, in particular UV light of a suitable wavelength. The spectral requirements can be controlled accordingly, if appropriate, by addition of suitable photosensitizers. Polymerization can be carried out in the presence or absence of a solvent. Suitable solvents are in principle all solvents which dissolve the monomers used, for example water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acteone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

If appropriate, a polymer network can be intensified by addition of a so-called crosslinking agent, for example a polyunsaturated comonomer (b). The invention furthermore relates to a polymer comprising the polymerization product of a macromer according to the invention with, ifappropriate, at least one vinylic comonomer (a) and with at least one comonomer (b). Examples of typical comonomers (b) are, for example, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate

EXAMPLES

| Monomer/Cat/Crosslinker | % | % | % | % | % | % |
|---|---|---|---|---|---|---|
| MMA | 25.5 | | | 24.2 | | |
| GMA | 68 | | | | | |
| HEMA | | | 93.25 | | 90 | 50 |
| NVP | | | | | | |
| VP | | | | 92.7 | | |
| MAA | | | | | 70 | 42 |
| TEDGMA | | | | | .5 | .75 |
| EDGMA | 1 | 1 | 1 | | 1 | |
| IPP | .2 | | | | | .2 |
| AIBN | | .25 | .3 | .3 | .25 | |
| PVA Fibers | 5.3 | | | | | 7.25 |
| PHEMA Fibers | | | 5.25 | 5 | | 8.75 |
| PVP Fibers | | | | | 5 | |

*IPP Isopropyl percarbonate
*AIBN azoisobutyronitrile

In each example above, electrospun fibers are made by dissolving 15% of the polymer in methanol and electrospinning the fibers as described previously. The weight of electrospun fiber is placed in a button mold, monomer composition from the table added, vacuum pulled on the solution, button mold top added, and polymerized at 60° C. in an oven for 24 hours followed by curing at 80° C. for 4 hours. The button removed and lens machined from the buttons by measuring hydration parameters on the polymerized materials.

Drug Delivery System Utilizing Electrospun Fibers

The electrospun fibers may be loaded with a therapeutic drug and utilized as a drug delivery system. The fibers can be used as inserts in the eye, either separately or as a mat. The insert can be placed in the cul-de-sac of the eye in the form of dry fibers or a mat of dry fibers. This dry mat placed in the eye will hydrate thereby releasing the therapeutic drug as the mat hydrates. The fibers can also be inserted under the conjunctiva or sclera and will slowly erode away releasing the therapeutic drug, provided the fiber is not a crosslinked polymeric material.

The fiber mats may be stored dry, as noted above, which will minimize the loss of the therapeutic drug during storage. This will require that residual impurities such as monomers be kept to a minimum and that hydration time will be short. The fiber mats may also be stored in water or another solvent, which will remove impurities from the fiber mats. The storage solution must also contain a sufficient concentration of the therapeutic drug to prevent the drug from dissolving from the fibers while in storage.

This drug delivery system provides for the release of ophthalmic drugs from the fiber mat to an eye over an extended period of time, thus improving the efficacy of the drug by maintaining a therapeutic concentration of the drug in the eye for a long period of time. Known methods of delivering drugs to an eye typically result in initially high concentrations of drugs that quickly drop to levels which are too low for optimal efficacy. The electrospun fibers in the drug delivery system may be loaded with appropriate drugs via several methods described below.

In a first method of loading the drug delivery system with appropriate drugs, the drugs are mixed with the polymer solution in the liquid well that feeds the electrospinning process. The concentration of the drug in the polymer solution will vary depending on the drug used and the rate and amount to dispensed from the fibers when in use in the eye, and will need to be determined experimentally or otherwise for each drug and polymer combination. Typically ranges of drug concentration in the polymer solution may range from 0.1% to 20% of the polymer solution. The drugs are dispensed with the polymer solution through the electrically-conducting liquid dispenser, and incorporated directly into the fibers created by the electrospinning process.

Polymer solutions for use in the drug delivery system include, but are not limited to, aqueous solutions having between 5 and 15 percent polymer by weight, similar to the base polymer solution utilized in the creation of the improved contact lens, with the addition of the therapeutic drug to be dispensed from the contact lens. The concentration of the drug in the contact lens and the rate of release in the eye are adjusted by altering the concentration of the drug in the polymer solution. More than one therapeutic drug may be added to the polymer solution to provide an improved contact lens that delivers a "cocktail" of drugs to the eye which may be tailored as necessary for the patient.

As an example of fiber mat formation, without limiting the range of parameters, mats for use with the drug delivery system described herein may be created by electrospinning PVA onto a flat rotating collector for 4 hours at a dispense rate of 1.8 ml per hour from an 18 gauge stainless steel needle situated 4 inches from the collector, and held at 30 kV DC from the collector. Varying the electrospinning time, the dispense rate, the needle gauge, the separation between dispenser and collector, and the dispenser potential are within the scope of the drug delivery system described herein, and the above described set of parameters is not limiting of the drug delivery system.

In a second method of loading the drug delivery matrix, the PVA mat is created, and then the mat is soaked in a solution containing the therapeutic drug. In this method, the therapeutic drug must be a water soluble drug. The amount of drug loaded into the fiber mat is dependent, among other parameters, on the soak time, the rate of uptake of the fibers, the fiber diameter, and the concentration of drug in the soak solution.

The rate of drug delivery from the fiber mats after placement in the eye is dependent, among other parameters, on the fiber diameter, the drug solubility in water, the amount of fiber in the mat (or lens), the amount of drug loaded in the fiber, and other parameters. The rate of drug delivery may also be controlled by changing the polymer composition from hydrophilic to hydrophobic, by treating the surface of the fibers to change the diffusion characteristics, by cross-linking the fibers and by coating the fibers with a polymer or other coating.

After the mats are created by electrospinning and subjected to drug-loading processing, if necessary, the mats may be coated with a polymer such as PVA by submersion in an aqueous solution of the polymer coating. They may also be crosslinked before and after the PVA coating.

An example of forming a fiber mat for drug delivery from electrospun fibers loaded with a therapeutic drug comprises the following steps. Dissolve 15% PVA in 5% moxifloxacin to methanol and electrospin into nanofibers. Place spun fibers in methanol containing 0.6% moxifloxacin for 2 hours and then dry the electrospun fibers. Form the spun fibers into a matt and store until use as an insert to place dry in the lower cul-de-sac of the eye.

A wide variety of therapeutic drugs may be spun into the fibers, so long as the drug is soluble in a solvent with the polymer solution. Examples of various types of drugs that may be spun into fibers include the following and any derivatives of the therapeutically-active agents which may include, but not be limited to: analogs, salts, esters, amines, amides, alcohols and acids derived from an agent of the invention and may be used in place of an agent itself.

Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), .beta.-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefininox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-$\beta$-d-glucosylsulfanilamide, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol).

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of the antineoplastic agents include, but are not limited to: antineoplastc antibiotics and analogs (e.g., aclacinomycins, actinomycin fsub.1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites exemplified by folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the non-steroidal anti-inflammatory agents include, but are not limited to: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, aldlofenac, amfenac, amtolmetin guacil, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lomoxicam, piroxicam, tenoxicam), E-acetamidocaproic acid, s-adenosylmethionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of anti-allergic agents include, but are not limited to: tranilast, ketotifen fumarate, pheniramine, diphenhydramine hydrochloride, sodium cromoglicate, bepotastine, epinastine HCl, olopatadine hydrochloride, levocombstine HCl, and bepotastine besilate.

Examples of glaucoma-treating agents include, but are not limited to: pilocarpine hydrochloride, carbocal, latanoprost, travoprost, bimatoprost, betaxolol, levobunalol, timolol, iganipidine, brinzolamide, brimonidine and isopropylunoprostone.

Examples of antiviral agents include, but are not limited to: idoxuridine, acyclovir, and trifluorouridine.

Examples of anti-mycotic agents include, but are not limited to: pimaricin, fluconazole, miconazole, amphotericin B, flucytosine, and itraconazole.

Formation of the Improved Contact Lens

Once the fiber mats have been produced, they are incorporated into a contact lens as it is manufactured. Acceptable contact lens polymers for use in the improved contact lens, include, but are not limited to polyHEMA, polyHEMA/MA, polyHEMA/NVP/MMA, polyHEMA/MMA, polyHEMA/GMA, polyHEMA/PC, polyVA, polyHEMA/PVP/MA, polyHEMA/PVA/MA, poly MA/PVP, and polyHEMA/PVP/MMA, Poly GMA/MMA, polyHEMA/ACR, polyAA/HEMA, polyMMA/AA, polysilicone hydrogel, polyfluorocarbon hydrogel, and collagen. The lens polymer is preferably a homo or co-polymer of the monomer used to form the fiber mat.

In one method of fabricating the improved contact lens, the lens is formed individually by curing a monomer composition in a mold to polymerize the composition and create the contact lens. The electrospun fiber mats is cut into appropriately-sized sections or ground into appropriately-sized particles, and incorporated into the contact lens by inserting the mat section into the mold with the monomer composition prior to polymerization. The fibers are then polymerized with the monomer composition and is incorporated into the improved contact lens. In a second method of fabricating an improved contact lens, the fibers may be polymerized into a button or rod of polymer material by inserting the fibers into the appropriate mold and curing with monomers. The button or rod is then processed by cutting or polishing to produce the final improved contact lens.

The improved contact lens has superior physical characteristics as a result of the addition of the electrospun fibers into the lens. The improved contact lens may be fabricated with a thinner cross-section due to the increased mechanical strength and rigidity of the electrospun fiber materials. The thinner cross-section of the lens provides increased oxygen permeability while maintaining mechanical strength.

Fibers loaded with therapeutic drugs as described above may be used to manufacture the improved contact lens. When forming a contact lens using fibers that have been loaded with a therapeutic drug, the polymerization conditions and other processing steps must be controlled to prevent degradation of the therapeutic drug.

An example of forming a contact lens from electrospun fibers loaded with a therapeutic drug comprises the following steps. Dissolve 15% polyacrylic acid and 5% tobramycin in methanol and electrospin polyacrylic acid fibers containing the antibiotic. Place these fibers in a button mold and add acrylic acid monomer, 1% EDGMA and 0.25% AIBN. Heat at 550 C. for 24 hours and cure at 850 C. for 2 hours. Remove from the mold and machine into a contact lens. Extract the residual monomers form the lens by placing in physiological saline containing 0.3% tobramycin for 24 hours. Remove from extract solution, replace with fresh 0.3% tobramycin physiological saline, autoclave at 1230 C and store until use.

The electrospun fiber mats may be incorporated into a contact lens using other methods of contact lens fabrication. The previous examples of contact lens fabrication are illustrative of current contact lens fabrication techniques and methods of incorporating the fiber mat into those methods of fabrication. They are not intended to be limiting of the present invention.

The desired concentration of therapeutic drug in the target tissue determines the amount of drug to be loaded in the improved contact lens. The target tissue concentration can be increased by adding additional fibers to the contact lens or by increasing the concentration of the therapeutic drug in the solution from which the fibers are spun.

Figure 1:
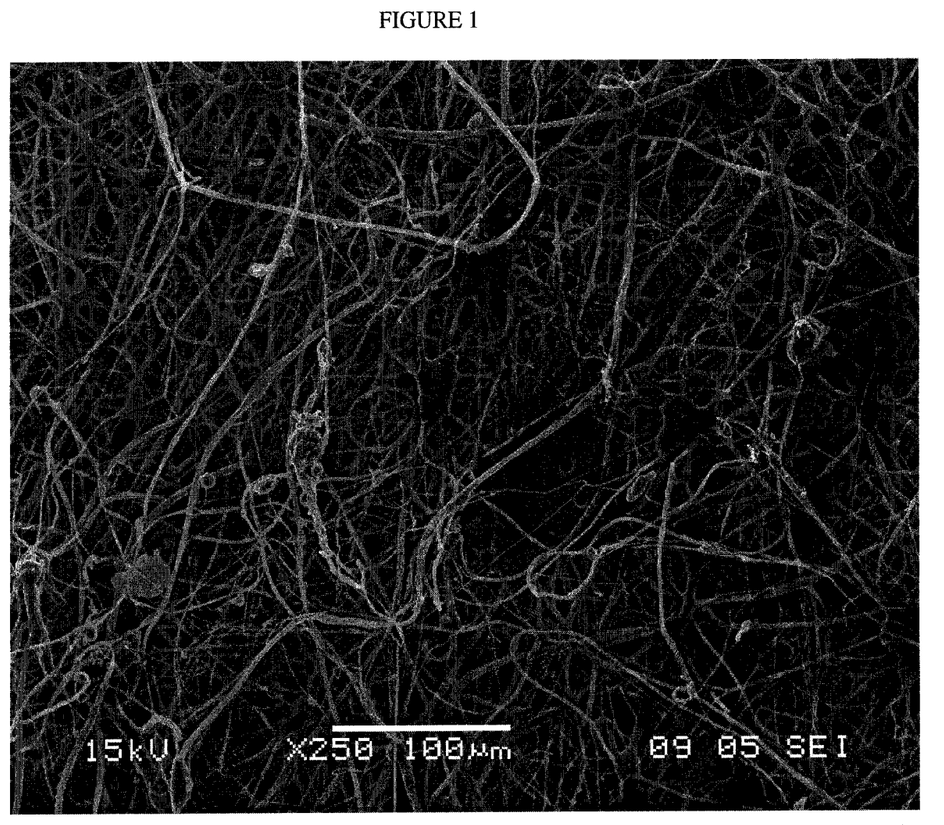
FIG. 1 is a scanning electron micrograph of a mat of fibers formed by electrospinning poly(vinyl) alcohol.

FIG. 1 is a scanning electron micrograph of a fiber mat created by electrospinning poly(vinyl alcohol). The fibers are deposited randomly throughout the mat in various orientations.

Figure 2:
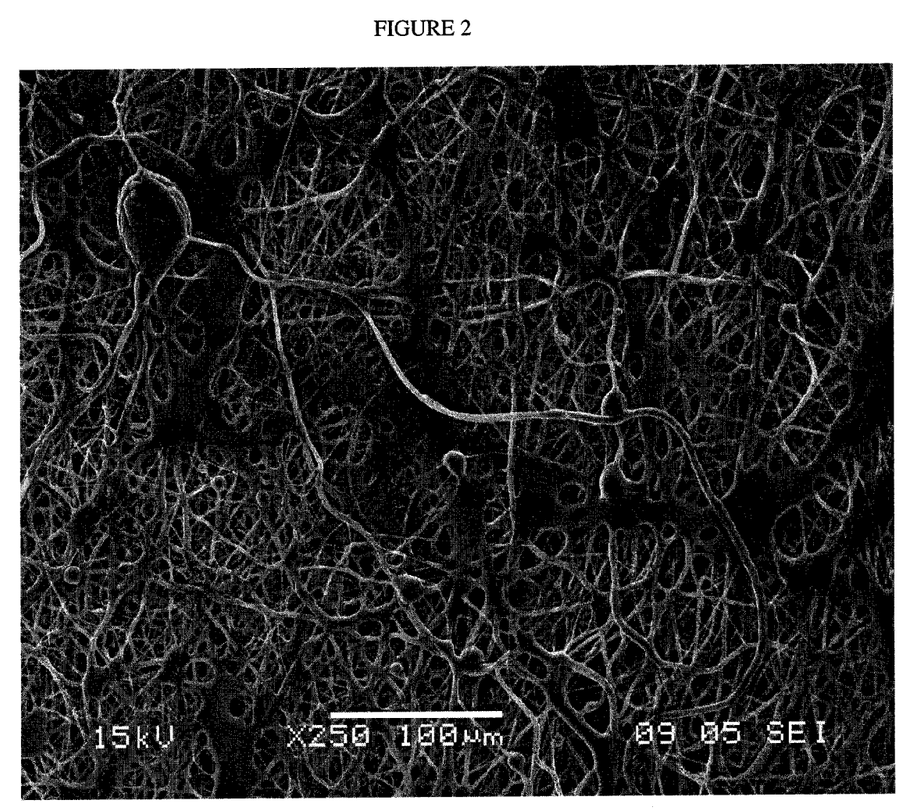
FIG. 2 is a scanning electron micrograph of a mat of fibers formed by electrospinning poly(vinyl) alcohol and crosslinked by submersion in methanol.

FIG. 2 is a scanning electron micrograph of a fiber mat created by electrospinning poly(vinyl alcohol) and crosslinking the resulting mat using methanol as a crosslinking agent. As can be seen in the figure, the fibers are linked at the intersection of overlapping fibers.

Figure 3:
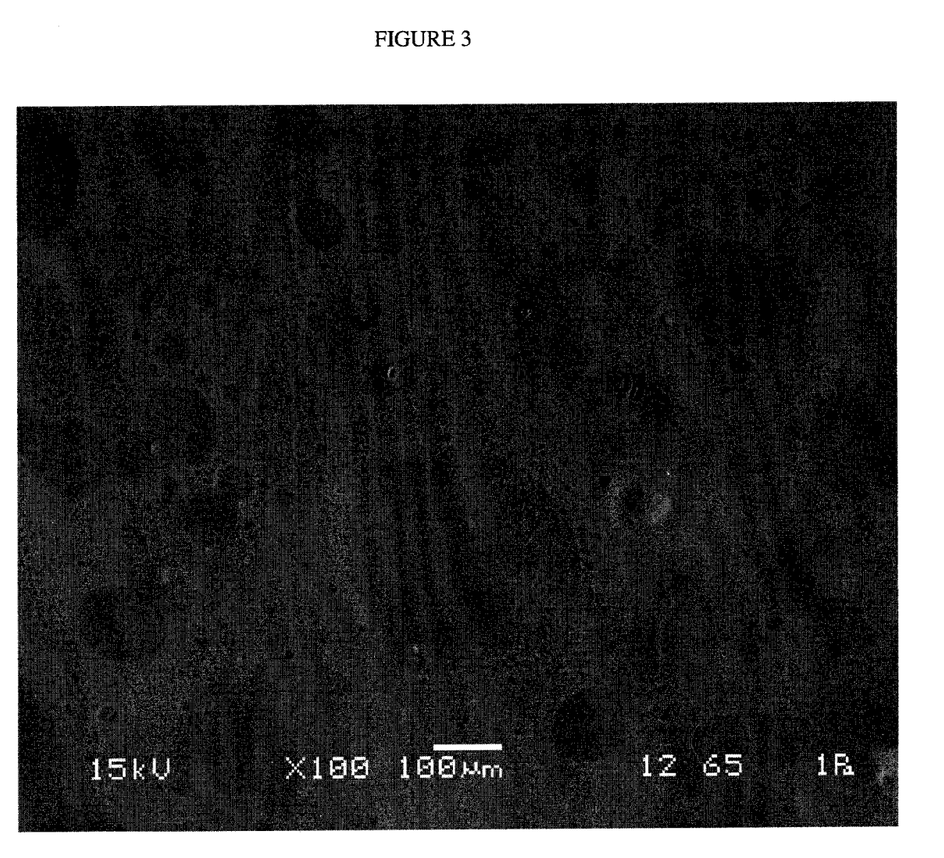
FIG. 3 is a scanning electron micrograph of a mat of fibers formed by electrospinning poly(vinyl) alcohol, crosslinked by submersion in methanol, coated with an aqueous solution of poly(vinyl) alcohol, and then crosslinked a second time.

FIG. 3 is a scanning electron micrograph of a fiber mat created by electrospinning poly(vinyl alcohol) and crosslinking the resulting mat using methanol as a crosslinking agent. The mat has then been coated with PVA and crosslinked a second time.

The fiber mats are tested for drug release properties by cutting the mats into small pieces and placing a piece into aqueous solution. The concentration of the drug in the solution is then measured over time. Since there is no mechanism in the solution for the removal of the drug, the concentration of the drug will increase over time to its maximum value. If the concentration remains constant, it indicates that the fiber mat is no longer releasing the drug.

Figure 4:
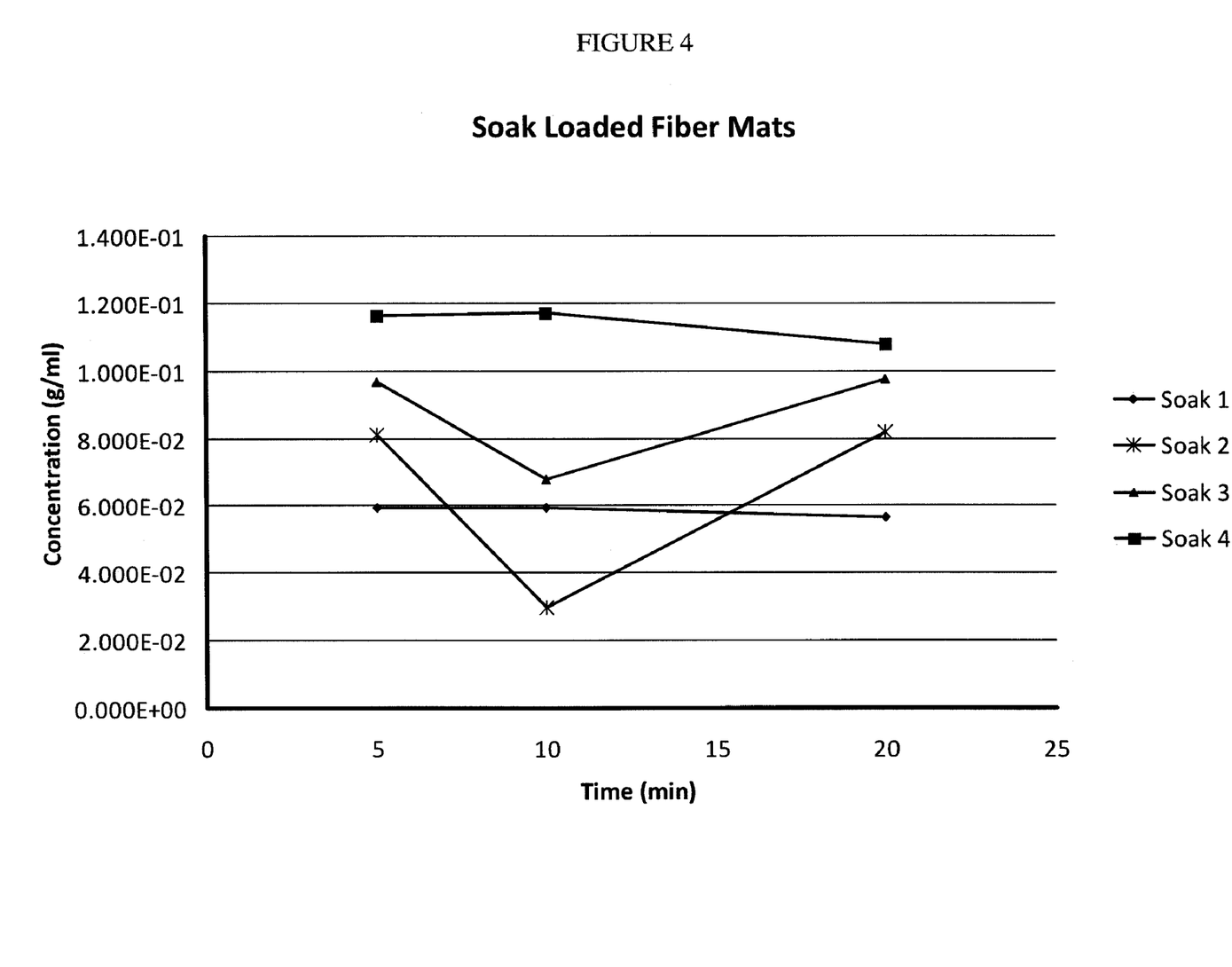
FIG. 4 is a graph of the concentration of a therapeutic drug released by a fiber mat soak-loaded with the therapeutic drug after deposition.

FIG. 4 is a graph of the concentration of a therapeutic drug released by a fiber mat soak-loaded with the therapeutic drug after deposition. The concentration of the drug released by the soak-loaded mat reached its maximum concentration within 5 minutes of the start of the drug release test. This indicates that the soak-loaded fiber mat quickly releases all of the drug that was loaded into the mat.

Figure 5:
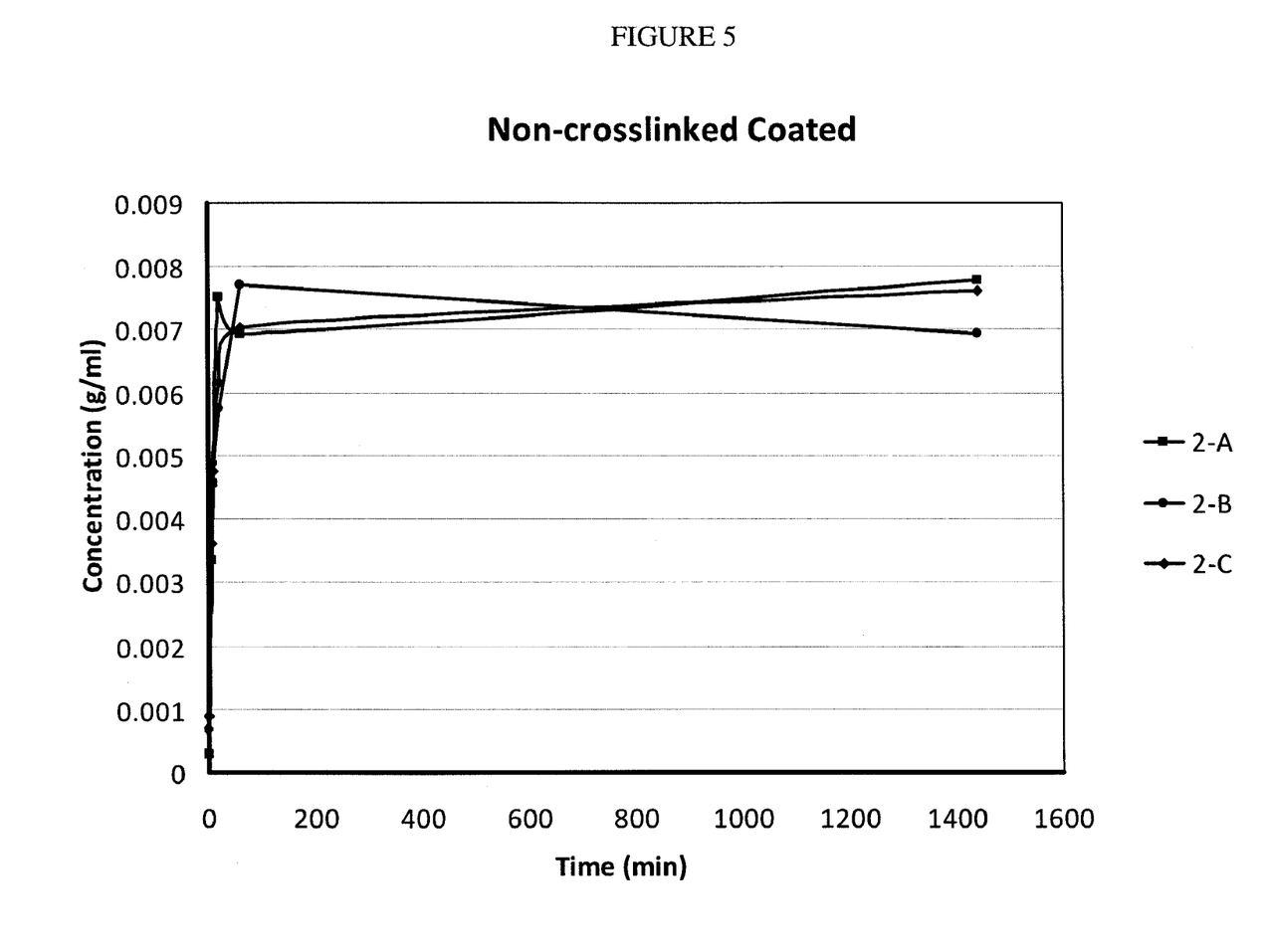
FIG. 5 is a graph of the concentration of a therapeutic drug released by a fiber mat fabricated from a precursor solution containing the therapeutic drug and coated with poly(vinyl) alcohol.

FIG. 5 is a graph of the concentration of a therapeutic drug released by a fiber mat fabricated from a precursor solution containing the therapeutic drug and coated with poly(vinyl alcohol). This figure shows that the concentration reaches its maximum value in the first hour, and thus that the fiber mat releases all the therapeutic drug within that time period.

Figure 5A:
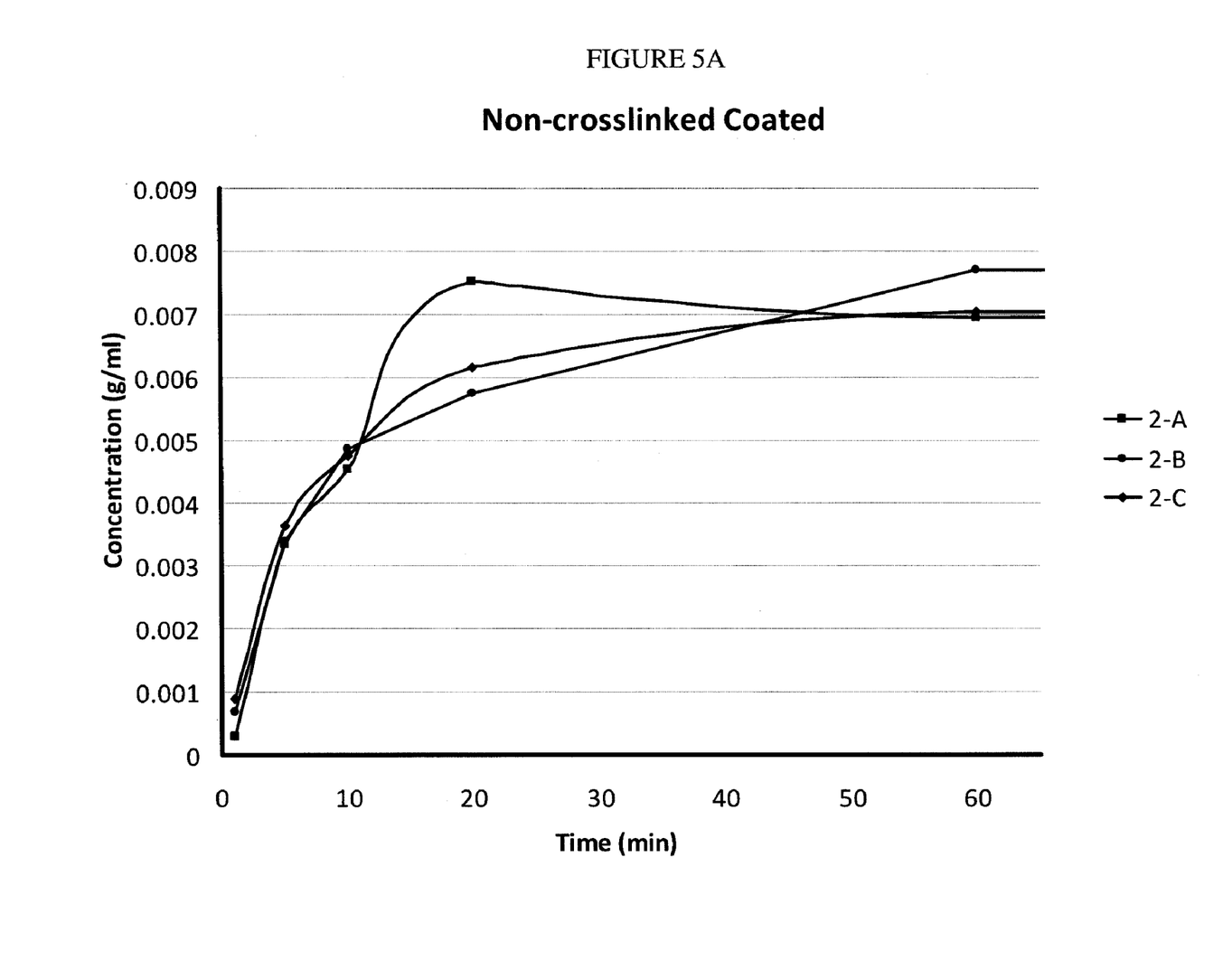
FIG. 5A is a graph of the first 60 minutes of the time period shown in FIG. 5.

FIG. 5A provides detail of the increasing concentration for the first hour of the test. It can be seen that the concentration increases over time, approaching its maximum value toward the end of the first hour.

Figure 6:
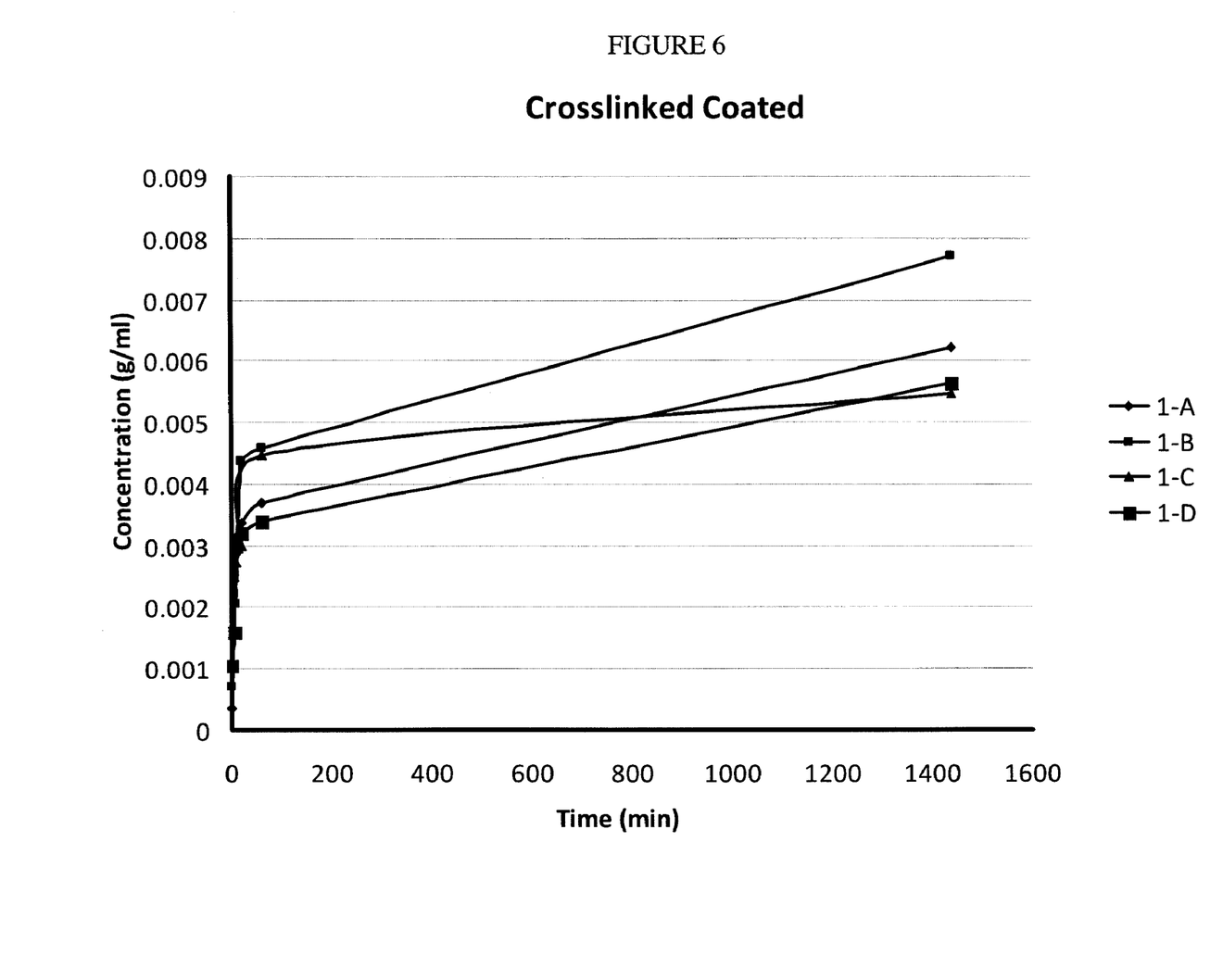
FIG. 6 is a graph of the concentration of a therapeutic drug released by a fiber mat fabricated from a precursor solution containing the therapeutic drug coated with poly(vinyl) alcohol, and crosslinked with methanol.

FIG. 6 is a graph of the concentration of a therapeutic drug released by a fiber mat fabricated from a polymer solution containing the therapeutic drug, coated with poly(vinyl alcohol), and crosslinked with methanol. This figure shows an increasing concentration throughout the time period of the test, revealing that the fiber mat in this test has continued to release the drug throughout the test period. The final maximum concentration is in the same range as for the mats shown in FIG. 5, however the drug was released over a much longer period of time.

Figure 6A:
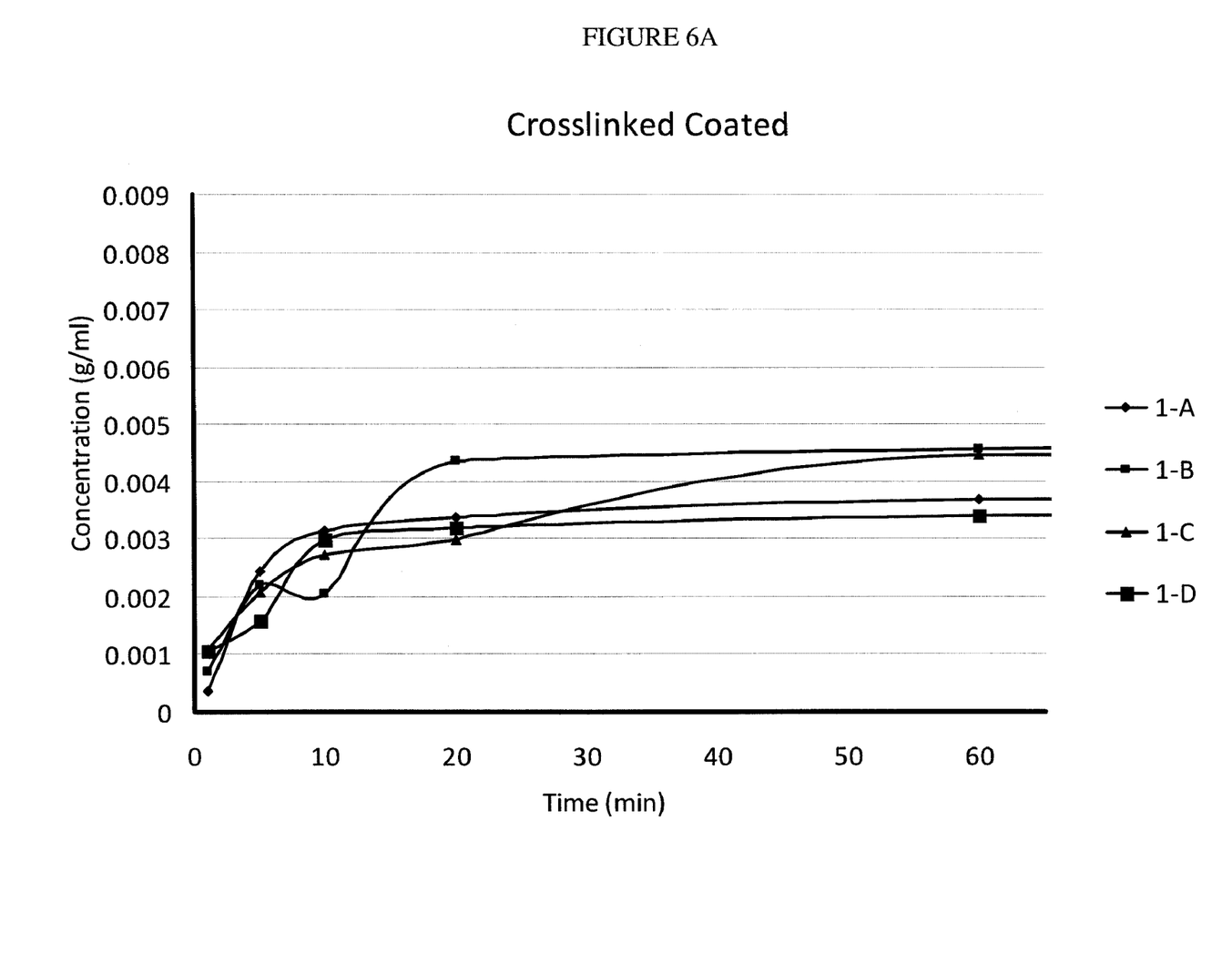
FIG. 6A is a graph of the first 60 minutes of the time period shown in FIG. 6.

FIG. 6A shows the detail of the initial 60 minutes of the test. This period of data indicates that the concentration initially quickly jumps and then begins a more steady increase over time, indicating that the fiber mat initially releases the drug quickly and then slows its rate of release over time.

What is claimed is:

1. A drug delivery system comprising:
    a contact lens comprising electrospun fibers incorporated into a polymer lens;
        wherein the electrospun fibers are prepared by electrospinning a polymer solution into a mat of fibers, applying a cross-linking treatment to the mat of fibers, and applying a polymer coating to the mat of fibers; and
    at least one therapeutic drug;
    wherein the at least one therapeutic drug is incorporated into the mat of fibers.

2. The drug delivery system of claim 1 wherein the at least one therapeutic drug is incorporated into the mat of fibers by soaking the mat of fibers in a solution containing the at least one therapeutic drug.

3. The drug delivery system of claim 1 wherein the at least one therapeutic drug is incorporated into the mat of fibers by spinning the mat of fibers from a solution containing the at least one therapeutic drug.

4. The drug delivery system of claim 3 wherein the solution contains at least one polymer selected from the group consisting of poly(2-hydroxyethylmethacrylate), poly(acrylic acid), poly(methacrylic acid), poly(vinyl pyrrolidone), poly (N-vinyl pyrrolidone), poly(vinyl alcohol), poly(methyl methacrylate), poly(glycerol methacrylate), silicone hydrogels, fluorocarbon hydrogels, polyacrylamide, polymers of silicone, polymers of (3-methacryloxy-2-hydroxypropyloxy) propyl-bis(trimethylsiloxy)methylsilane, polymers of C3-C18alkyl and C3-C18cycloalkyl acrylates and methacrylates, polymers of C3-C18alkylacrylamides and -methacrylamides, polyacrylonitrile, polymethacrylonitrile, polymers of vinyl C1-C18alkanoates, polymers of C2-C18alkenes, polymers of C2-C18haloalkenes, polystyrene, poly-lower alkyl styrene, polymers of lower alkyl vinyl ethers, polymers of C2-C10perfluoroalkyl acrylates and methacrylates or correspondingly partly fluorinated acrylates and methacrylates, polymers of C3-C12perfluoroalkyl-ethyl-thiocarbonylaminoethyl acrylates and methacrylates, polymers of acryloxy- and methacryloxy-alkylsiloxanes, poly(N-vinylcarbazole), polymers of C1-C12alkyl esters of maleic acid, poly(fumaric acid), poly(itaconic acid), poly(mesaconic acid), polymers of C1-C4alkyl esters of vinylically unsaturated carboxylic acids having 3 to 5 carbon atoms, polymers of vinyl esters of carboxylic acids having up to 5 carbon atoms, poly(methyl acrylate), poly(ethyl acrylate), poly(propyl acrylate), poly (isopropyl acrylate), poly(isobutyl acrylate), poly(isooctyl acrylate), poly(isodecyl acrylate), poly(cyclohexyl acrylate), poly(2-ethylhexyl acrylate), poly(ethyl methacrylate), poly (propyl methacrylate), poly(butyl acrylate), poly(vinyl acetate), polyvinyl propionate), poly(vinyl butyrate), poly (vinyl valerate), poly(chloroprene), poly(vinyl chloride), poly(vinylidene chloride), polymers of 1-butene, polybutadiene, poly(vinyl toluene), poly(vinyl ethyl ether), polymers of perfluorohexylethylthiocarbonylaminoethyl methacrylate, poly(isobornyl methacrylate), polymers of trifluoroethyl methacrylate, polymers of hexafluoroisopropyl methacrylate, polymers of hexafluorobutyl acrylate, polymers of hexafluorobutyl methacrylate, polymers of tris-trimethylsilyloxy-silyl-propyl methacrylate, polymers of 3-methacryloxypropylpentamethyldisiloxane, polymers of bis(methacryloxypropyl) tetramethyldisiloxane, polymers of hydroxyl-substituted lower alkyl acrylates and methacrylates, polymers of lower alkylacrylamides and -methacrylamides, polymers of ethoxylated acrylates and methacrylates, polymers of hydroxyl-substituted lower alkylacrylamides and -methacrylamides, polymers of hydroxyl-substituted lower alkyl vinyl ethers, poly(sodium vinylsulfonate), poly(sodium styrenesulfonate), polymers of 2-acrylamido-2-methylpropanesulfonic acid, poly(N-vinylpyrrole), poly(N-vinyl-2-pyrrolidone), polymers of 2-vinyloxazoline, polymers of 2-vinyl-4, 4'-dialkyloxazolin-5-one, poly(2-vinylpyridine), poly(4-vinylpyridine), polymers of vinylically unsaturated carboxylic acids having a total of 3 to 5 carbon atoms, polymers of amino-lower alkyl (where the term "amino" also includes quaternary ammonium), polymers of mono-lower alkylamino-lower alkyl and di-lower alkylamino-lower alkyl acrylates and methacrylates, poly(allyl alcohol), polymethacrylamide, polymers of hydroxyl-substituted lower alkyl acrylates and methacrylates, hydroxyethyl methacrylate, poly(hydroxyethyl acrylate), poly(hydroxypropyl acrylate), poly(dimethylaminoethyl methacrylamide), poly(yinylpyridine), poly(glycerol methacrylate), polymers of N-(1, 1dimethyl-3-oxobutyl)acrylamide, poly (dimethylaminoethyl methacrylate), polymers of trimethylammonium-2-hydroxypropyl methacrylate hydrochloride, poly(N,N-dimethylacrylamide) and mixtures thereof.

5. The drug delivery system of claim 3 wherein the solution contains between 5 and 15 percent polymer by weight.

6. The drug delivery system of claim 5 wherein the concentration of the at least one therapeutic drug in the solution is between 0.01% and 20%.

7. The drug delivery system of claim 3 wherein the mat of fibers is soaked in a cross-linking agent.

8. The drug delivery system of claim 7 wherein the mat of fibers is coated with a polymer coating.

9. The drug delivery system of claim 8 wherein the mat of fibers is soaked in a cross-linking agent after application of the polymer coating.

10. The drug delivery system of claim 1 wherein the mat of fibers is incorporated into the contact lens by inserting the mat of fibers into a button or rod mold in which the contact lens is formed and polymerizing the contact lens around the mat of fibers.

11. The drug delivery system of claim 10 wherein the mat of fibers is ground into particles before being placed into the mold.

12. The drug delivery system of claim 1 wherein the at least one therapeutic drug is selected from the group consisting of antibacterial antibiotic drugs, synthetic antibacterial drugs, antifungal antibiotic drugs, synthetic antifungal drugs, antineoplastic agents, steroidal anti-inflammatory agents, non-steroidal anti-inflammatory agents, anti-allergic agents, glaucoma-treating agents, antiviral agents and anti-mycotic agents.

13. The drug delivery system of claim 12 wherein the antibacterial antibiotic drugs are selected from the group consisting of aminoglycosides, amikacin, apramycin, arbekacin, bambermycins, butirosin, dibekacin, dihydrostreptomycin, fortimicins, gentamicin, isepamicin, kanamycin, micronomicin, neomycin, neomycin undecylenate, netilmicin paromomycin, ribostamycin, sisomicin, spectinomycin, streptomycin, tobramycin, trospectomycin, amphenicols, azidamfenicol, chloramphenicol, florfenicol, thiamphenicol, ansamycins, rifamide, rifampin, rifamycin sv, rifapentine, rifaximin, beta.-lactams, carbacephems, loracarbef, carbapenems, biapenem, imipenem, meropenem, panipenem, cephalosporins, cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin, cephamycins, cefbuperazone, cefmetazole, cefininox, cefotetan, cefoxitin, monobactams, aztreonam, carumonam, tigemonam, oxacephems, flomoxef, moxalactam, penicillins, amdinocillin, amdinocillin pivoxil, amoxicillin, ampicillin, apalcillin aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin, ritipenem, lincosamides, clindamycin, lincomycin, macrolides, azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin, polypeptides, amphomycin, bacitracin, capreomycin, colistin, enduracidin, enviomycin, fusafungine, gramicidin s, gramicidins, mikamycin, polymyxin, pristinamycin, ristocetin, teicoplanin, thiostrepton, tuberactinomycin, tyrocidine, tyrothricin, vancomycin, viomycin, virginiamycin, zinc bacitracin, tetracyclines, apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline, cycloserine, mupirocin, and tuberin.

14. The drug delivery system of claim 12 wherein the synthetic antibacterial drugs are selected from the group consisting of 2,4-diaminopyrimidines, brodimoprim, tetroxoprim, trimethoprim, nitrofurans, furaltadone, furazolium chloride, nifuradene, nifuratel, nifurfoline, nifurpirinol, nifurprazine, nifurtoinol, nitrofurantoin, quinolones and analogs, cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin, sulfonamides, acetyl sulfamethoxypyrazine, benzylsulfamide, chloramine-b, chloramine-t, dichloramine t, n.sup.2-formylsulfisomidine, n.sup.4-.beta.-d-glucosylsulfanilainide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, n.sup.4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole, sulfones, acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone, clofoctol, hexedine, methenamine, methenamine anhydromethylene-citrate, methenamine hippurate, methenamine mandelate, methenamine sulfosalicylate, nitroxoline, taurolidine, and xibornol.

15. The drug delivery system of claim 12 wherein the antifungal antibiotic drugs are selected from the group consisting of polyenes, amphotericin b, candicidin, dennostatin, filipin, fungichromin, hachimycin, hamycin, lucensomycin, mepartricin, natamycin, nystatin, pecilocin, perimycin, azaserine, griseofulvin, oligomycins, neomycin undecylenate, pyrrolnitrin, siccanin, tubercidin, and viridin.

16. The drug delivery system of claim 12 wherein the synthetic antifungal drugs are selected from the group consisting of allylamines, butenafine, naftifine, terbinafine, imidazoles, bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole, thiocarbamates, tolciclate, tolindate, tolnaftate, triazoles, fluconazole, itraconazole, saperconazole, terconazole, acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

17. The drug delivery system of claim 12 wherein the antineoplastic agents are selected from the group consisting of antineoplastic antibiotics, aclacinomycins, actinomycin f.sub.1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin, antimetabolites, folic acid analogs, denopterin, edatrexate, methotrexate, piritrexim, pteropterin, Tomudex.RTM., trimetrexate, purine analogs, cladribine, fludarabine, 6-mercaptopurine, thiamiprine, thioguanine, pyrimidine analogs, ancitabine, azacitidine, 6-azauridine, carmofur, cytarabine, doxifluridine, emitefur, enocitabine, floxuridine, fluorouracil, gemcitabine, and tagafur.

18. The drug delivery system of claim 12 wherein the steroidal anti-inflammatory agents are selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

19. The drug delivery system of claim 12 wherein the non-steroidal anti-inflammatory agents are selected from the group consisting of aminoarylcarboxylic acid derivatives, enfenamic acid, etofenamate, flufenamic acid, isonixin, meclofenamic acid, mefenamic acid, niflumic acid, talniflumate, terofenamate, tolfenamic acid, arylacetic, acid derivatives, aceclofenac, acemetacin, alclofenac, amfenac, amtolmetin guacil, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac, arylbutyric acid derivatives, bumadizon, butibufen, fenbufen, xenbucin, arylcarboxylic acids, clidanac, ketorolac, tinoridine, arylpropionic acid derivatives, alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen, pyrazoles, difenamizole, epirizole, pyrazolones, apazone, benzpiperylon, feprazone, mofebutazone, morazone, oxyphenbutazone, phenylbutazone, pipebuzone, propyphenazone, ramifenazone, suxibuzone, thiazolinobutazone, salicylic acid derivatives, acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine, thiazinecarboxamides, ampiroxicam, droxicam, isoxicam, lomoxicam, piroxicam, tenoxicam, E-acetamidocaproic acid, s-adenosylmethionine, 3-amino-4-hydroxybutyric acid, amixetrine, bendazac, benzydamine, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

20. The drug delivery system of claim 12 wherein the anti-allergic agents are selected from the group consisting of tranilast, ketotifen fumarate, pheniramine, diphenhydramine hydrochloride, sodium cromoglicate, bepotastine, epinastine HCl, olopatadine hydrochloride, levocombstine HCl, and bepotastine besilate.

21. The drug delivery system of claim 12 wherein the glaucoma-Treating agents are selected from the group consisting of pilocarpine hydrochloride, carbocal, latanoprost, travoprost, bimatoprost, betaxolol, levobunalol, timolol, iganipidine, brinzolamide, brimonidine and isopropylunoprostone.

22. The drug delivery system of claim 12 wherein the antiviral agents are selected from the group consisting of idoxuridine, acyclovir, and trifluorouridine.

23. The drug delivery system of claim 12 wherein the anti-mycotic agents are selected from the group consisting of pimaricin, fluconazole, miconazole, amphotericin B, flucytosine, and itraconazole.

24. The drug delivery system of claim 3 wherein the solution contains the polymer polyvinyl alcohol.

25. The drug delivery system of claim 1 wherein the at least one therapeutic drug is a steroidal anti-inflammatory agent.

* * * * *